United States Patent
Haseltine et al.

(10) Patent No.: US 6,620,043 B1
(45) Date of Patent: Sep. 16, 2003

(54) VIRTUAL TUG OF WAR

(75) Inventors: Eric C. Haseltine, Burbank, CA (US); Kyle W. Poor, Clermont, FL (US); John W. Sogge, Orlando, FL (US)

(73) Assignee: Disney Enterprises, Inc., Burbank, CA (US)

(*) Notice: Subject to any disclaimer, the term of this patent is extended or adjusted under 35 U.S.C. 154(b) by 0 days.

(21) Appl. No.: 09/493,390

(22) Filed: Jan. 28, 2000

(51) Int. Cl.[7] ............................................. A63F 13/00
(52) U.S. Cl. ................... 463/7; 463/1; 463/8; 463/40; 463/41; 463/42; 700/90; 700/91; 700/92; 273/317.1; 273/358; 273/129 V; 273/148 R; 273/444; 273/451; 273/453
(58) Field of Search .................. 463/7, 1, 8, 29, 463/30, 31, 34, 35, 40, 41, 42, 43, 46, 47, 59, 64, 66, 67; 700/90, 91, 92; 273/317.1, 358, 129 V, 148 R, 148 B, 440.1, 444, 451, 452, 453

(56) References Cited

U.S. PATENT DOCUMENTS

| | | | |
|---|---|---|---|
| 1,676,755 A | * 7/1928 | Walton | 273/441 |
| 2,884,248 A | 4/1959 | Tenney | |
| 3,301,555 A | * 1/1967 | Sicherman | 273/451 |
| 3,913,914 A | * 10/1975 | Cooper | 273/244 |
| 4,346,884 A | * 8/1982 | Warehime | 273/451 |
| 4,572,511 A | 2/1986 | Barringer | |
| 4,627,617 A | * 12/1986 | Gilmore et al. | 482/131 |
| 4,674,741 A | 6/1987 | Pasierb, Jr. et al. | |
| 4,828,253 A | * 5/1989 | Schicketanz | 482/906 |
| 4,919,416 A | * 4/1990 | DeCloux | 482/53 |
| 5,213,555 A | * 5/1993 | Hood et al. | 482/57 |
| 5,284,459 A | * 2/1994 | Podd, III | 482/51 |
| 5,318,491 A | 6/1994 | Houston | |
| 5,363,297 A | * 11/1994 | Larson et al. | 342/126 |
| 5,466,200 A | 11/1995 | Ulrich et al. | |
| 5,495,576 A | * 2/1996 | Ritchey | 345/420 |
| 5,542,672 A | 8/1996 | Meredith | |
| 5,645,513 A | * 7/1997 | Haydocy et al. | 482/3 |
| 5,713,792 A | 2/1998 | Ohzono et al. | |
| 5,713,794 A | * 2/1998 | Shimojima et al. | 434/253 |
| 5,730,655 A | 3/1998 | Meredith | |
| 5,813,945 A | 9/1998 | Bernacki | |
| 5,888,172 A | 3/1999 | Andrus et al. | |
| 6,004,243 A | * 12/1999 | Ewert | 434/247 |
| 6,090,019 A | * 7/2000 | Price, II | 482/148 |
| 6,227,974 B1 | * 5/2001 | Eilat et al. | 273/148 B |
| 6,244,988 B1 | * 6/2001 | Delman | 482/8 |

* cited by examiner

Primary Examiner—Valencia Martin-Wallace
Assistant Examiner—Binh-An D. Nguyen
(74) Attorney, Agent, or Firm—The Hecker Law Group

(57) ABSTRACT

The present invention provides a novel form of entertainment in which participants compete in a "tug of war" against opponents who are remotely located, stored in electronic form in memory, or are virtual opponents graphically generated in real-time by a computer. One embodiment implements "tug of war" in a manner compatible with international standards for Tug competitions. The invention consists of a rope attached to a motor to supply a counterforce to the pulling team. A tensiometer is attached to the rope to determine the force being applied to the rope by the pulling team. In one embodiment, there is a corresponding assembly being used by an opposing team and in data communication with the first assembly. The motor applies a counterforce to the rope being pulled by one team based on the force being applied by the other team to their own rope. In this manner, the system works as if the teams were each pulling on the same rope.

1 Claim, 7 Drawing Sheets

VIRTUAL TUG OF WAR

BACKGROUND OF THE INVENTION

1. Field of the Invention

This invention relates to the field of entertainment and active participation activities.

Portions of the disclosure of this patent document contain material that is subject to copyright protection. The copyright owner has no objection to the facsimile reproduction by anyone of the patent document or the patent disclosure as it appears in the Patent and Trademark Office file or records, but otherwise reserves all copyright rights whatsoever.

2. Background Art

The game of tug of war is an ancient sporting activity that pits the strength and endurance of one opponent against another. The opponents can be individuals, teams, or any combination thereof. The rules of the game are relatively simple. Two teams pull on opposite ends of a rope in opposing directions. A marker of some sort, such as a flag or colored tape, is placed on the rope approximately halfway between the two teams. The object is for one team to pull the rope so that the marker moves over some designated point some distance away from the starting point. This distance can be of any length, but in some international rules, the distance is twelve feet. Typically the contestants are only allowed to move the rope by moving their feet. Pulling the rope in a "hand over hand" manner is prohibited. Once the marker has been moved beyond the designated point, the contest is over.

Tug of war is growing in popularity. The International Olympic Committee has recently granted recognition to the Tug of War International Federation (TWIF) making the organization eligible to join the Association of Recognized International Sports Federations. This is a preliminary step to qualifying as an Olympic competition. There are sanctioned teams and tournaments throughout the world and annual world championship events.

Although equipment costs are relatively low for the sport (requirements are a rope and markers), there are a number of problems that prevent the sport from wider participation. One is that a relatively large space is required for play. In some competitions, the teams each consist of eight members and the rope used is 150 feet long. Another problem is the weather dependency of the sport. Although it can be played in wet conditions, it is difficult, and in extreme cold or snowy conditions, play may not be possible at all.

Another problem associated with tug of war is the risk of injury. If a teammate drops the rope or loses footing, the other team gains an immediate pulling advantage. This sudden advantage can result in the rope being suddenly pulled through the hands in a rapid manner, with friction burns and even loss of fingers being real consequences. In addition, a sudden change in direction can result in injury causing falls, pulled muscles, dislocated joints, and even broken limbs.

Another problem with tug of war is the inability to adapt it to a an indoor environment as a vended entertainment. It is also often difficult to obtain opponents without traveling. Finally, there currently is no good manner of solo or single team practicing or competing.

SUMMARY OF THE INVENTION,

The present invention seeks to create a novel form of entertainment in which participants compete in a "tug of war" against opponents who are remotely located, stored in electronic form in memory, or are virtual opponents graphically generated in real-time by a computer. One embodiment implements "tug of war" in a manner compatible with international standards for tug of war in a manner compatible with international standards for tug of war competitions, such as rope length, team composition, etc.

Another embodiment of this invention permits the play of teams that are remotely located or, if a communication link is not available, or a remotely located opponent is not available, to still play tug of war and compare their performance against other participants.

The invention consists of a rope attached to a motor to supply a counterforce to the pulling team. A tensiometer is attached to the rope to determine the force being applied to the rope by the pulling team. In one embodiment, there is a corresponding assembly being used by an opposing team and in data communication with the first assembly. The motor applies a counterforce to the rope being pulled by one team based on the force being applied by the other team to their own rope. In this manner, the system works as if the teams were each pulling on the same rope. The motor assembly includes sensors to detect any sudden change in the force being applied to its own rope or the rope of the other team. If the sudden change in force could result in a dangerous condition, such as overspeed of the rope in one direction, the motor provides appropriate tension to prevent accidents.

The invention contemplates embodiments where there are two assemblies, each being used by one team, and where the two teams compete with each other. The assemblies may be in the same geographical location or may be located at any distance apart, so long as a suitable communication path exists to transfer data between assemblies. In other embodiments, a single assembly can be used for competitions between a human team and a virtual team. In other embodiments, a human team may compete against the stored results of another human team, where the former team is simulated by the assembly.

To further enhance the virtual tug of war experience, cameras are used to transmit images of opposing teams to displays at each assembly so that the illusion of two teams pulling the same rope is achieved. Microphones and speakers can be used to permit the teams to communicate orally to each other.

DETAILED DESCRIPTION OF THE INVENTION

The invention is a method and apparatus for providing virtual tug of war. In the following description, numerous specific details are set forth to provide a more thorough description of embodiments of the invention. It will be apparent, however, to one skilled in the art, that the invention may be practiced without these specific details. In other instances, well known features have not been described in detail so as not to obscure the invention.

Figure 1:
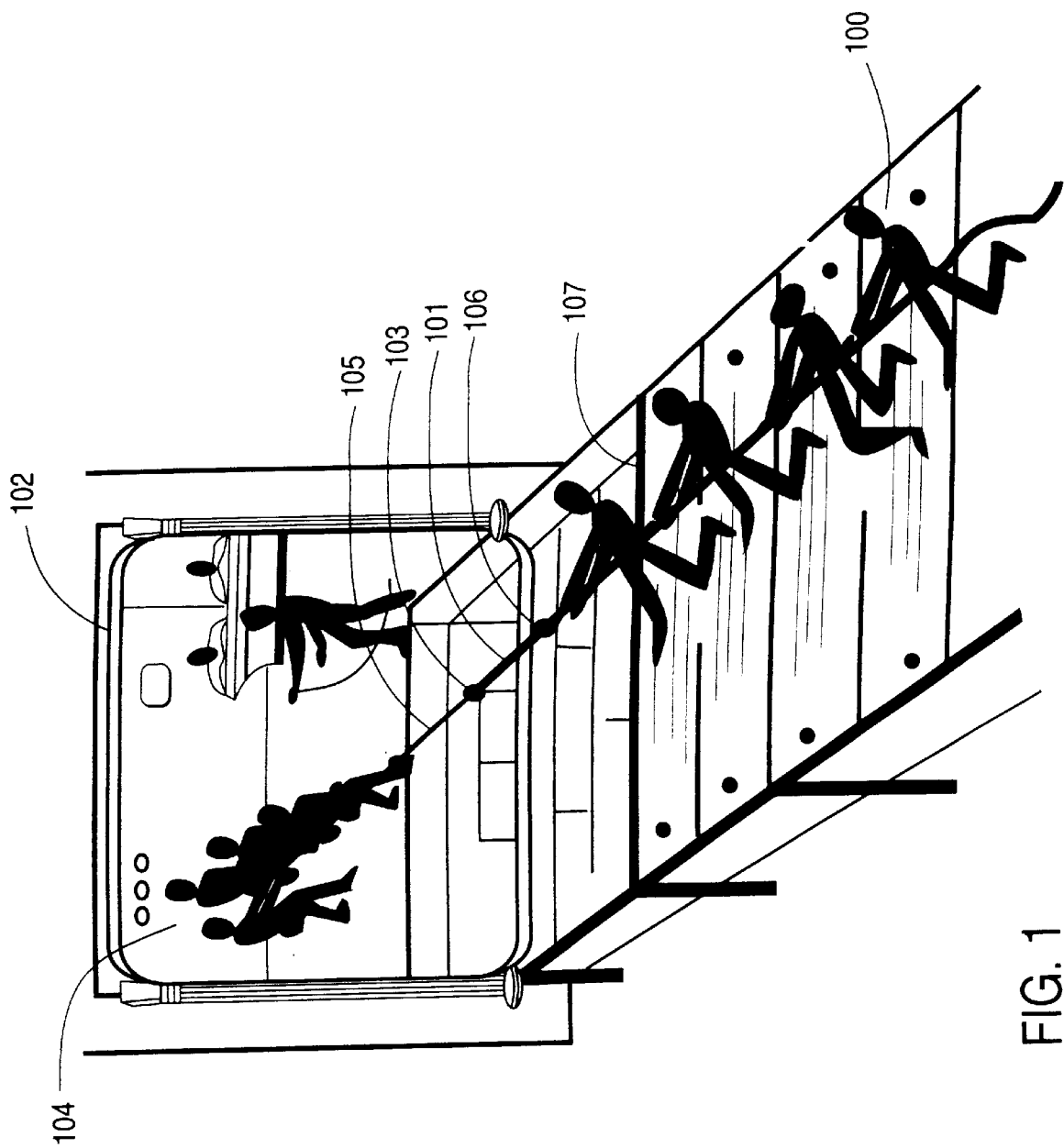
FIG. 1 illustrates a perspective view of one embodiment of the present invention in operation.

FIG. 1 illustrates a perspective view of one embodiment of the present invention in operation. A first team, team 100, is competing in tug of war against a second team, team 104. Team 100 is in a different location than team 104. A display screen 102 is used to display a live picture of team 104 at team 100's location. Team 100 pulls on rope 101 which passes through display 102 at opening 103. The rope 101 is attached to a motor (not shown in FIG. 1) that provides a counterforce based on the pulling force of team 104 on their rope 105. Correspondingly, rope 105 of team 104 is attached to a motor at the location of team 104 that provides a counterforce on rope 105 based on the pulling force of team 100. A camera at the location of team 104 broadcasts a live picture to display 102 so that it appears that teams 100 and 104 are pulling on a single rope and are in physical proximity. In fact, the teams are at different locations and pulling on two different ropes.

When team 100 pulls harder than the team 104, the counterforce on rope 101 lessens and increases on rope 105. This allows team 100 to appear to "pull" team 104 toward them, and correspondingly move the marker 106 past the designation point 107 and win the contest. The system is reactive in that the counterforce on each rope changes based on the relative pulling force applied by the opposite team.

Figure 2:
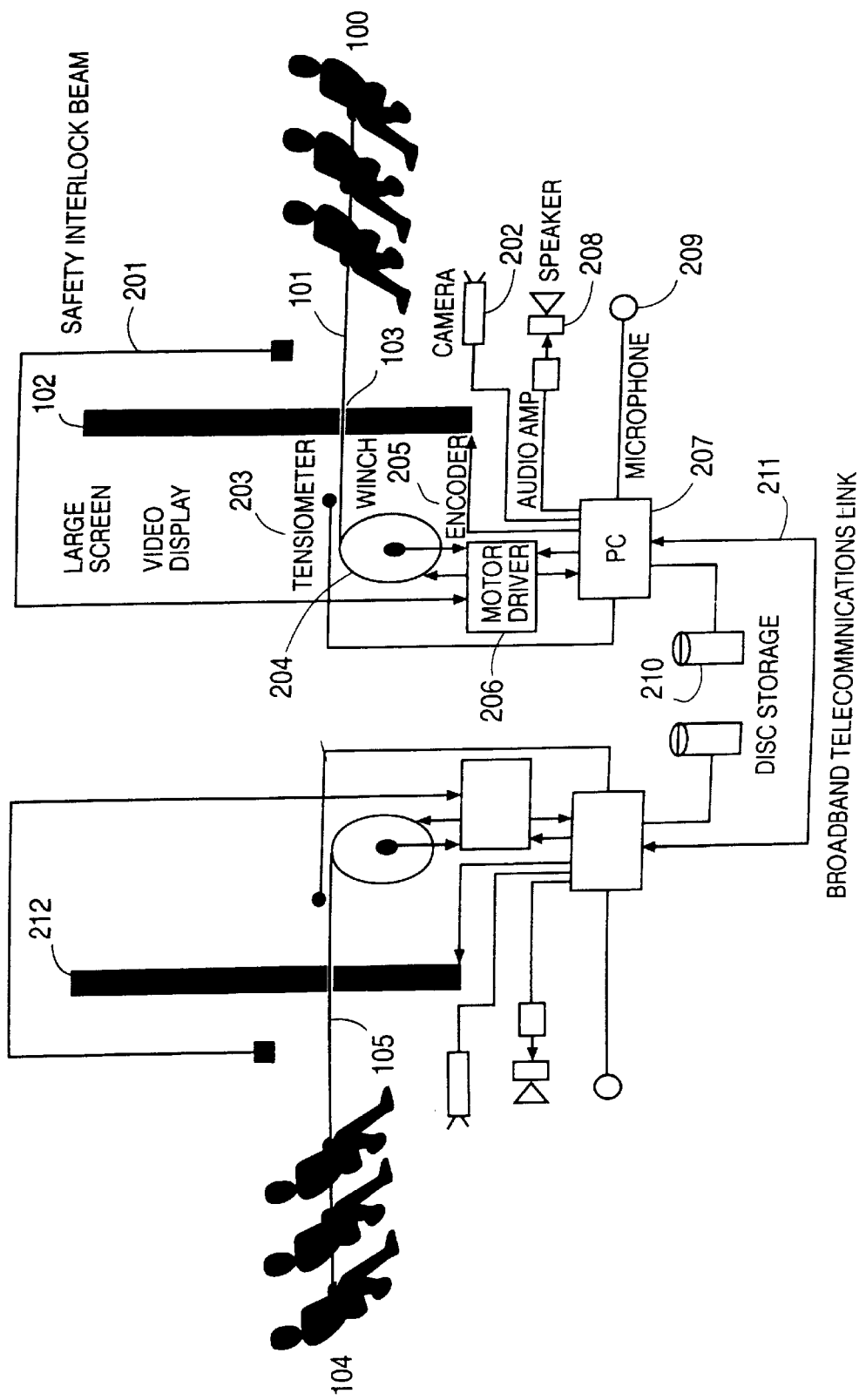
FIG. 2 is a block diagram illustrating an embodiment of the invention.

FIG. 2 is a block diagram illustrating an embodiment of the present invention. Team 100 is shown pulling rope 101 that extends through opening 103 in display 102. The rope 101 is coupled to a winch 204 mounted behind the display 102. The winch is controlled by a motor driver 206 that determines the counterforce applied to the rope 101 by the winch 204. The motor assembly features a reduction gear which, in conjunction with the RPM chosen for the motor, insures that an overspeed condition does not cause excessive force to be exerted on the rope. A tensiometer 203 is also coupled to the rope 101 to provide a signal to computer 207 that represents the amount of force being applied to the rope 101 by team 100. The computer 207 provides appropriate control signals to motor driver 206 so that appropriate counterforce is generated via winch 204. An example of a suitable computer 207 would be a Compaq XX NT with a 300 MHZ CPU, 64 MB of memory, with a 9 Gbyte hard disc, Diamond Multi-media Card with video and stereo audio outputs, IEEE 422 instrumentation interface, 3Dfx Voodo graphics generator, MPEG 2 Real Time Code, and ATM interface for broadband data communications. However, any suitable computer system can be used without departing from the scope and spirit of the present invention.

A camera 202 is used to transmit an image of team 100 to the display 212 facing team 104. A microphone 209 can be used to pick up team and/or crowd noises and transmit them to the other location. A speaker 208 is used to broadcast audio from the other location or to broadcast prerecorded audio if desired. Computer 207 includes disk storage 210 for storing virtual team data and images or for storing other human team data. A telecommunications link 211 can be created between one location and another for distributed team play. The telecommunications link may be a broadband communications link, such as satellite transponder or broadband telephone line. This same telecommunications link is used to transmit tensiometer data between sites.

In operation team 100 at one location pulls on rope 101 that passes through video display 102 (via opening 103) to an electric winch 204 that applies a countering force on the rope 101. A tensiometer 203 attached to a wire leading from the rope to the motor sends tension data to computer 207. Computer 207 uses the input to help determine the amount of torque it will command the electric winch—through a motor controller—to exert. The computer 207 also transmits the data from its location to a remote location, and receives tensiometer data from the remote location. The computer 207 uses the inputs from the remote tensiometer/computer assembly at the remote location to determine the torque commands of the motor at this location. In this manner, the motor at each site exerts a force corresponding to the tension applied on the rope by the opposing team. The result is as if the teams were actually pulling on the same rope.

An optical beam sensor system 201 located in front of display 102 shuts off the motor driver if an object or individual is pulled too close to the video display 102 or otherwise enters a region close to the front of display 102.

Computer 207 may include a graphics generator for creating text and graphics that are mixed with the video prior to display on the video screen. These text and graphics display, for example, may include computed scores and team rankings of different teams, and other data relevant to the experience.

To avoid casting of shadows of the rope onto the screen, the preferred mode of video display is a self luminous display such as LED video display or fiber optic video display. These display devices also lend themselves to incorporating a hole for passage of the rope.

Figure 3:
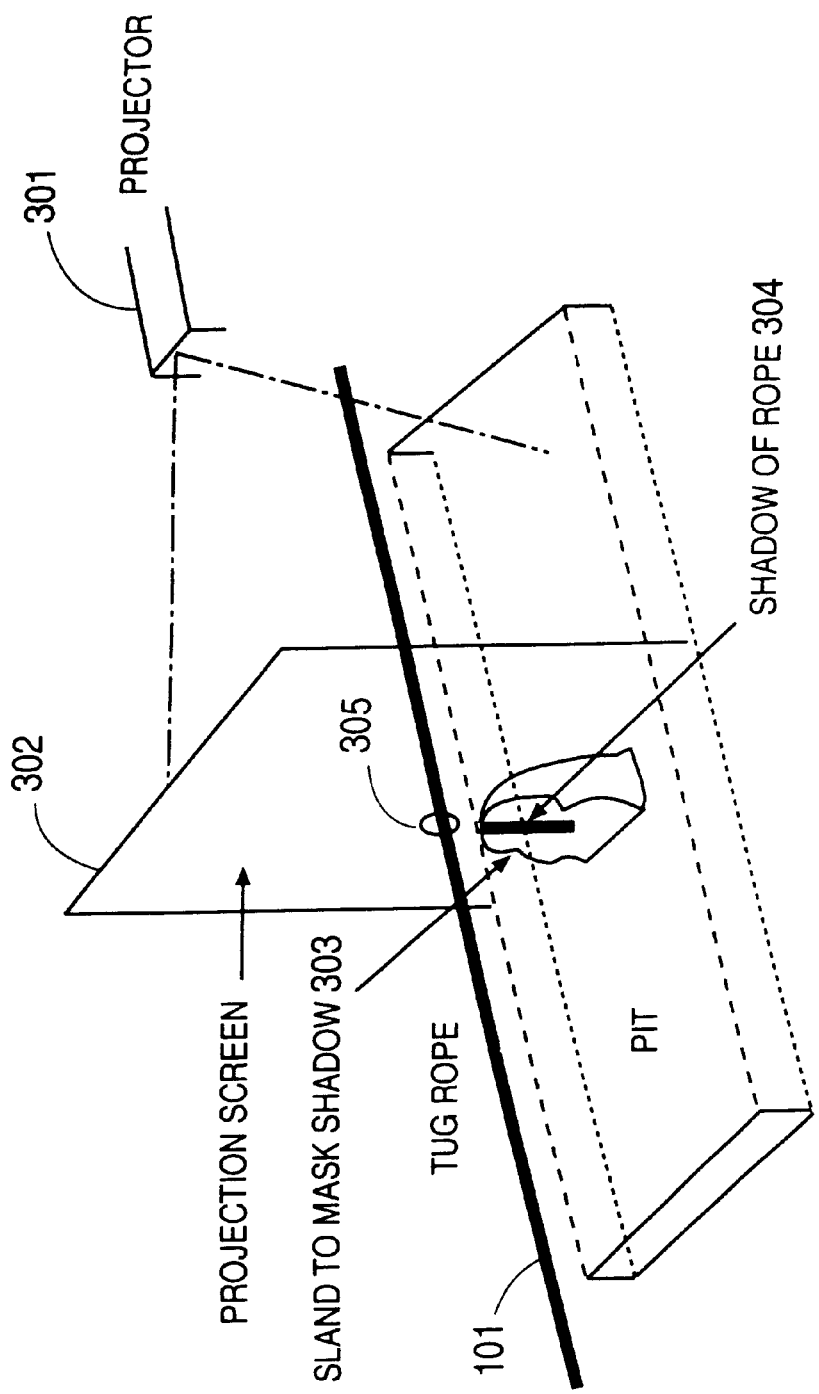
FIG. 3 illustrates an alternate embodiment of the invention.

In another embodiment, a front or rear projection system featuring a hole in the projection screen to pass the rope may be used. In such a system, steps should be taken to disguise the shadow cast, from either side of the projection screen, by the rope or mechanical assemblies attached to the rope. One technique for hiding this shadow is shown in FIG. 3. A projector 301 projects images on rear projection screen 302. An opening 305 in screen 302 is provided for the rope 101 to pass through. When the projector 301 is on, the light emitted can cast a shadow 304 of rope 101 onto the screen 302 below opening 305. To mask the shadow of the rope (or other equipment in the bath of the light from projector 301, a physical feature, such as an island 303, can be placed in front of the screen 302 so that the shadow is not seen.

Figure 4:
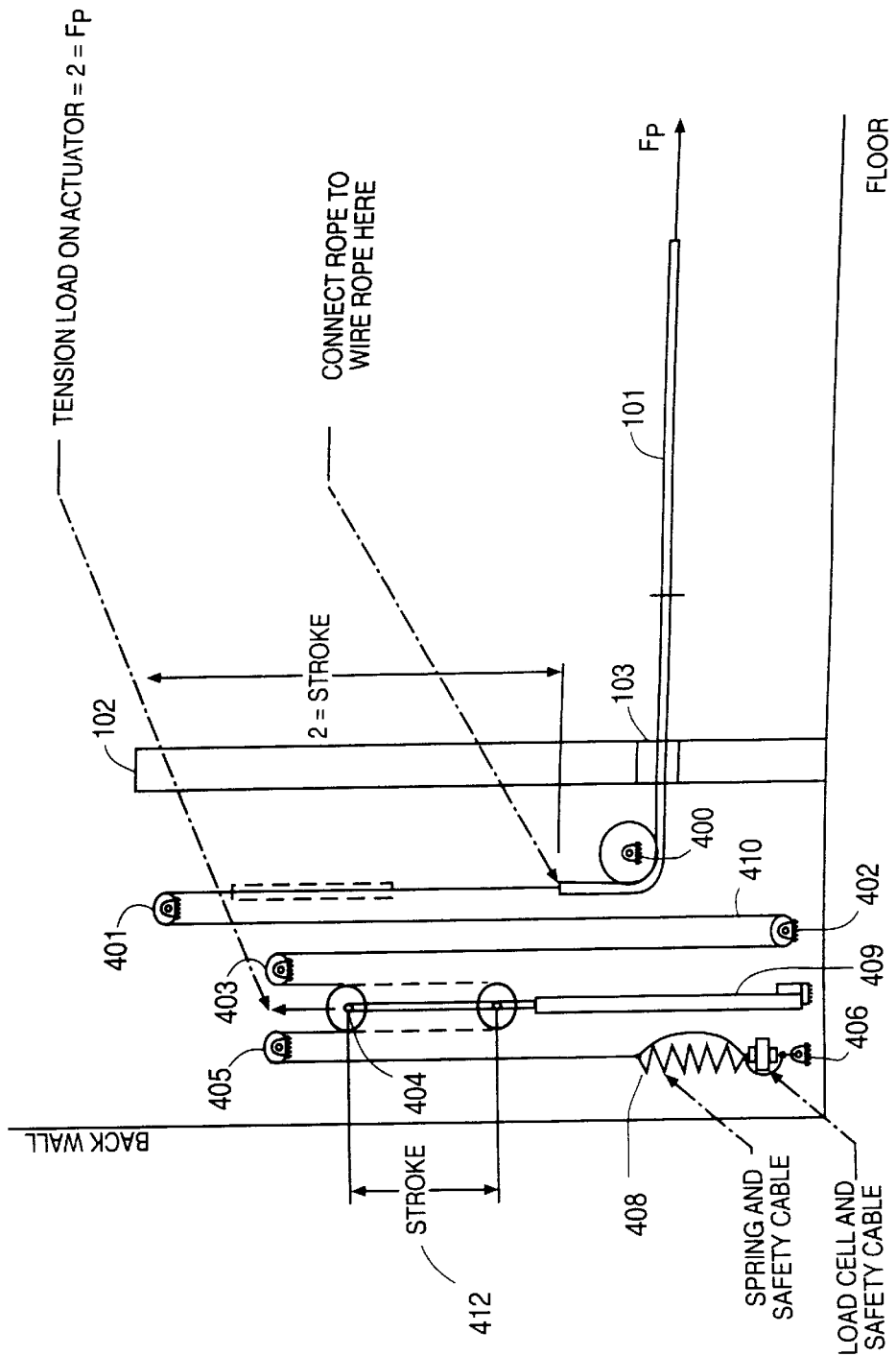
FIG. 4 illustrates a pulley arrangement for rope take-up in an alternate embodiment of the invention.

To provide a realistic experience, the rope should be of adequate length. This can be achieved by having the rope spooled on the winch as indicated in FIG. 2. In an alternate embodiment, the rope can be attached to a pulley system as shown in FIG. 4. Referring to FIG. 4, rope 101 passes through opening 103 of display 103 and around winch pulley 400. The rope is then connected to a wire 410 and the wire passes over pulley 401 and is coupled to pulley 402. Wire 411 is then positioned over pulley 403, under movable pulley 404, over pulley 405, and mounted via spring and safety cable assembly 408 (with an optional load cell assembly) to mount 406. A tension load system 409 is coupled to one side of moveable pulley 404 to provide a tension force to rope 101. The tension load system 409 permits movement of pulley 404 through a stroke distance 412. The tension load system is biased to pull the moveable pulley 404 down and must be offset by a pulling force on the rope 101.

Operating Environments

Local Mode—The present invention can be used in a "local" mode, where there is no live opponent during operation, and no need for a link to another system during the operation. There are several variations of local mode operation. In one mode, video images of one or more opponents at the same station or at remote stations are stored in memory or on the disk storage 210 of the computer 207. When a local team wants to have a match, a stored replay of one of the stored teams is presented on the display 102 as opponents. The playback of the stored team is read out in forward or reverse at a rate that depends on the difference between the force exerted by the participants and the computed force profile stored in the computer's memory for the stored opponent. Sound effects that correlate with the video recording of the opponent may be played back through the audio-amplifier/speaker assembly. The stored image of the opponent can be taken from an actual match against a live team or from an opponent competing against a virtual team. The stored opponent can even be the same team itself from a previous experience.

In another local mode of operation, the team competes against a "virtual" team from the computer memory. This virtual team could be video of live competitors stored in the memory of the system, it could be animated computer graphics, or it could be a real time rendered image of a synthetic character that pulls on a virtual rope, (also rendered by the graphics generator). The force profile could be the same each time or it could be randomly assigned. In other embodiments, the competitors can select a "degree of difficulty" and compete against a virtual opponent with a desired force profile.

In the case of a rendered opponent, for example, the graphics generator could animate a simulated 3D alligator (stored as a 3D database in the graphics generator's memory) tugging with its jaws on a synthetic 3D rope. The computer computes motor drive commands based upon the difference between a stored force profile for the alligator and the actual force exerted by the contestants. Similarly, the behavior of the 3D alligator (e.g. whether it pulls away from or towards the participants) will depend on the force exerted by the participants. Synthetic sound effects from the tugging gator would also be generated as appropriate in the computer's sound card and broadcast over loudspeakers through the audio amplifiers and speakers.

Figure 5:
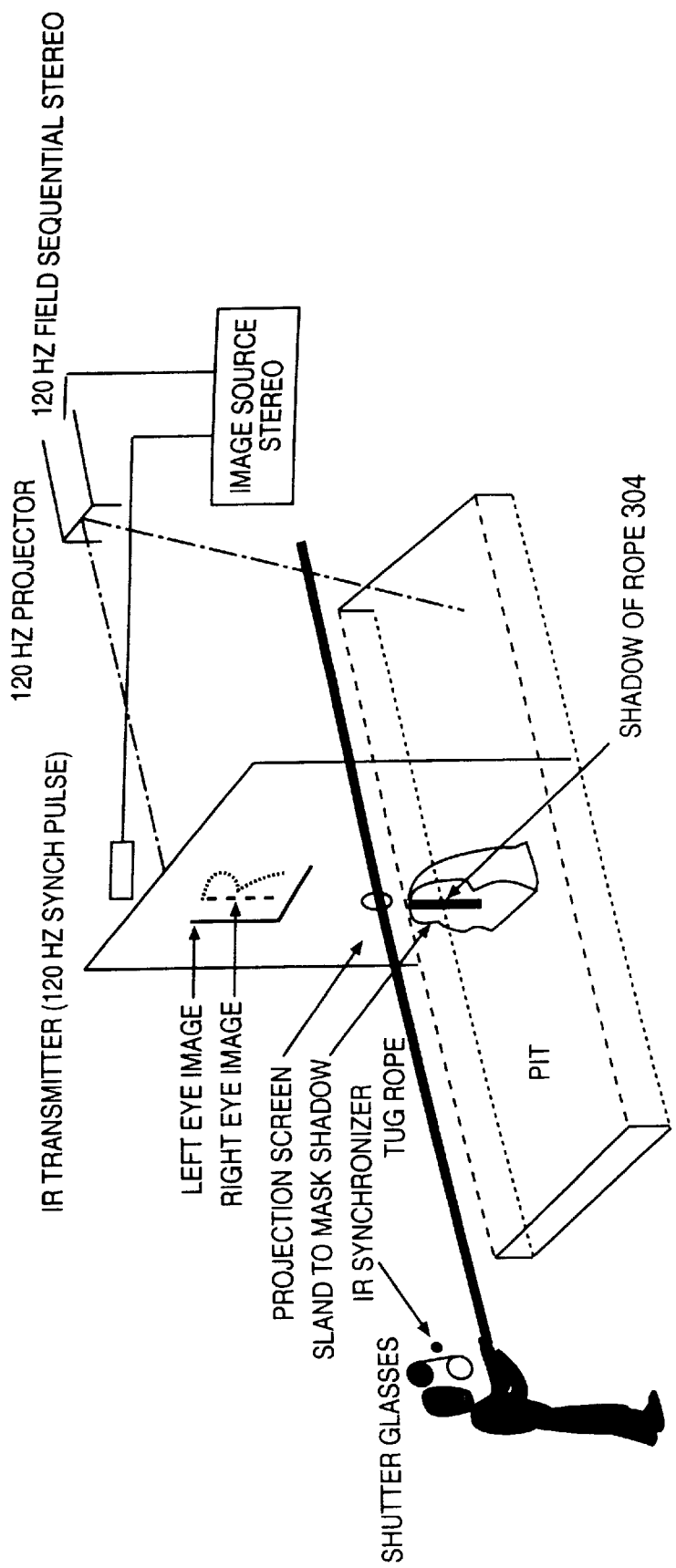
FIG. 5 illustrates another embodiment of the present invention.

In another embodiment of the invention, shown in FIG. 5, a stereo visual image of the telepresent or virtual opponents is displayed on the video screen. The preferred mode for stereo display is field sequential presentation, in which images for left and right eyes, developed from two cameras (in the case of the live or stored video images), or from two computed view windows (in the case of the computer generated simulated opponents), are alternately displayed in different halves of a 60 HZ frame, and decoded via synchronized shuttered glasses 600 worn by each participant. Alternate methods of stereo display, such as dual projectors with orthogonal polarization, can be used in the present invention.

Figure 7:
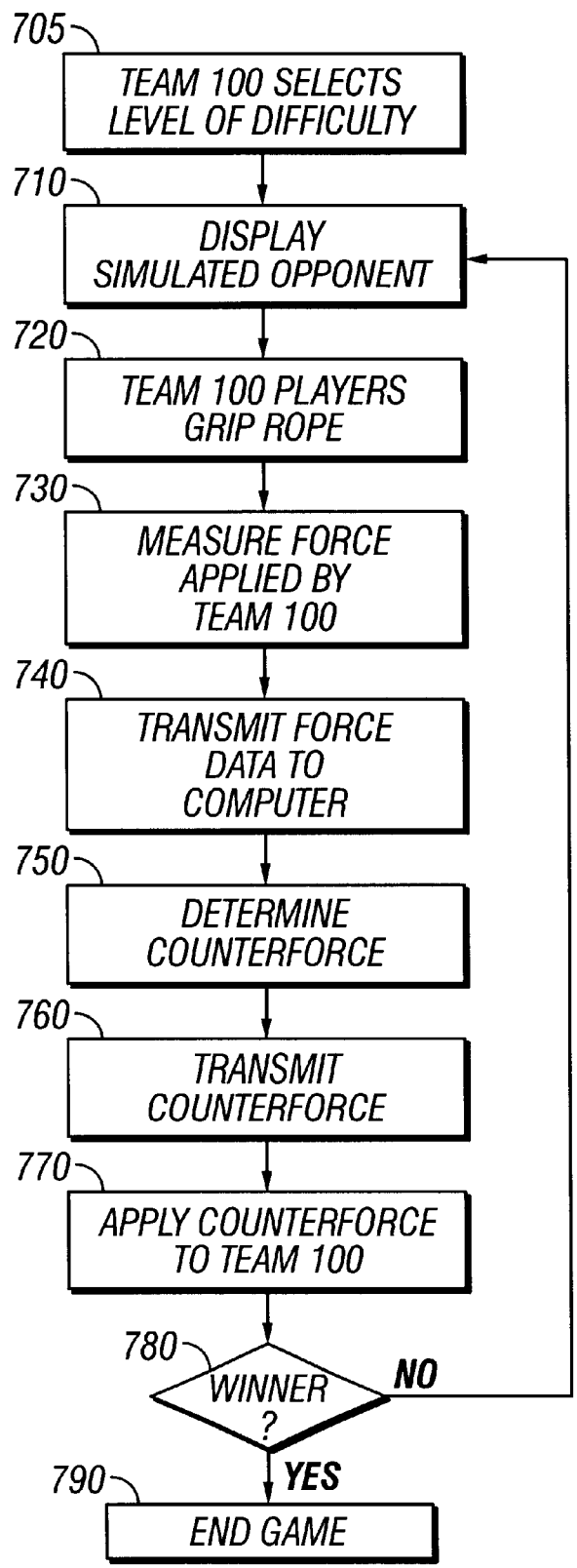
FIG. 7 is a flow diagram of one embodiment of the invention illustrating the method where a first team is competing in tug of war against a virtual team.

FIG. 7 is a flow diagram of one embodiment of the invention illustrating the method where a first team, team 100, is competing in tug of war against a virtual team. Team 100 selects the level of difficulty of the virtual team, or simulation, at step 705. A display screen 102 is used to display a picture of a virtual, or simulated, team at team 100's location as indicated by step 710. At step 720, team 100 players grip and pull on rope 101. At step 730, the force applied by team 100 to rope 101 is measured by tensiometer 203. At step 740, a signal is provided by tensiometer 203 to a computer 207 that transmits the force data from the tensiometer. This computer uses the input to help determine the amount of torque it will command the electric winch, through a motor controller, to exert. At step 750, computer 207 determines the counterforce to be provided on rope 101 representing the virtual team. At step 760, computer 207 transmits the counterforce data to the motor controller and motor. At step 770, the motor applies a counterforce to rope 101 held by team 100 based on the computer determination. If one side has won at step 780, the process ends at step 790. If there is no winner at step 780, the process is repeated beginning at step 710.

Remote Mode—In the remote mode of operation, a telecommunications link is established between a local tug of war assembly and a second tug of war assembly. The second assembly need not be remotely located, but may even be in the same establishment. The system is such that the assemblies could be side by side, but due to the camera display assemblies, the contestants appear to be pulling in opposing directions. The remote mode requires that some method of initiating the contest be provided. Both teams must be in a ready position before the contest can begin. This can be accomplished by providing appropriate graphics on the display, such as "waiting for opponents" or a countdown to begin the match. Of course, the camera system permits the opponents to know when each team is present and ready.

Both the local and remote operation of the systems can be coin operated, where participants pay for one or more matches. Such a vended system has particular application in establishments such as taverns, sports clubs, malls, etc. In addition to team play, single player play can be provided where a single real or virtual opponent is provided. Alternatively, a plurality of choices may be provided and the user selects one from a menu. Solo or team competition is also contemplated where an individual or team attempts to meet certain limits of pulling force or length of time. The individual or team can attempt to better marks set previously on the assembly.

Figure 6:
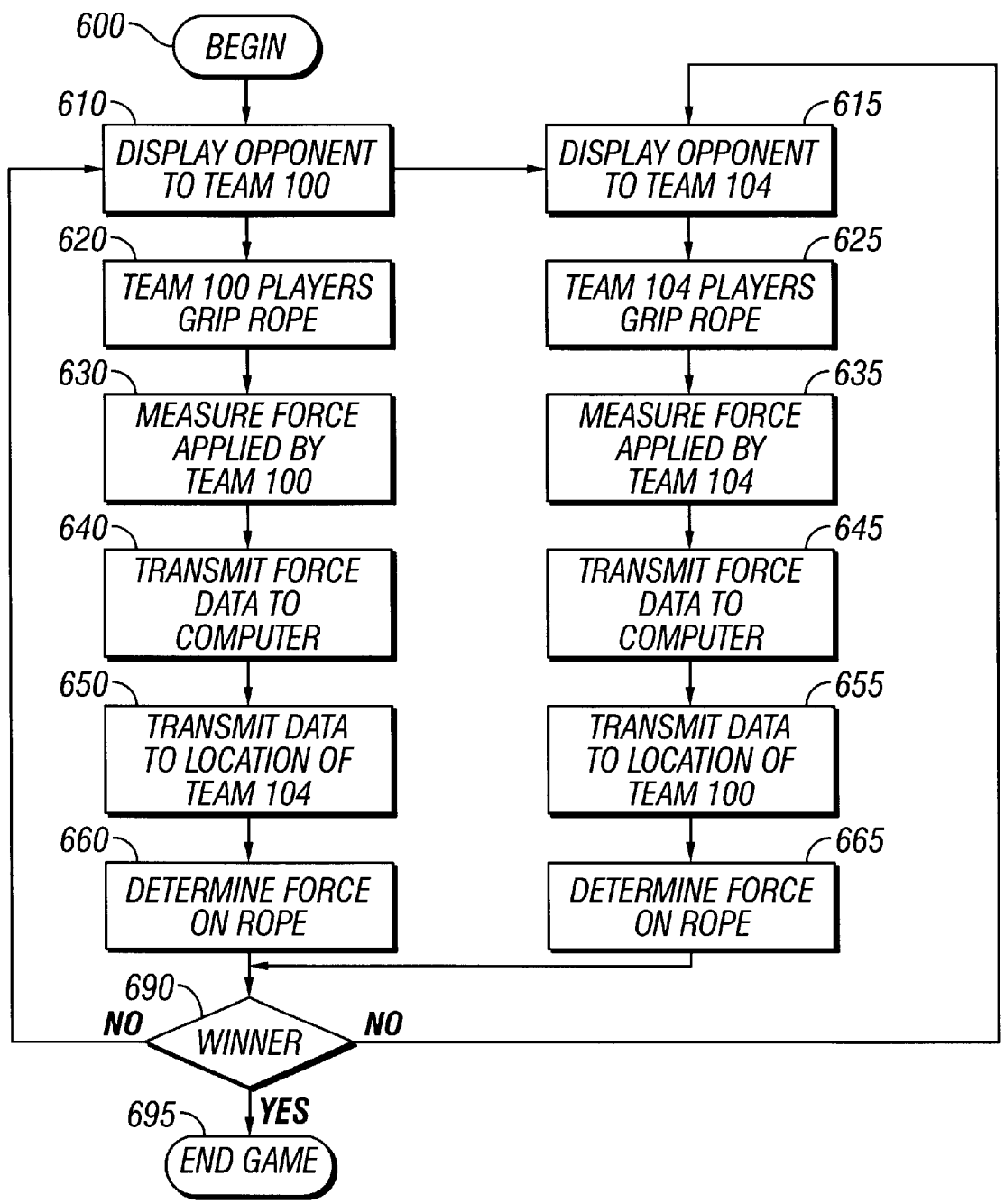
FIG. 6 is a flow diagram of one embodiment of the invention illustrating the method whereby two teams play with each other at different sites.

FIG. 6 is a flow diagram of one embodiment of the invention illustrating the method, beginning at step 600, whereby two teams play with each other at different sites. A first team, team 100, as discussed earlier, is competing in tug of war against a second team, team 104. Team 100 is in a different location than team 104. A display screen 102 is used to display a picture of team 104 at Team 100's location as indicated by step 610 of FIG. 6. A similar display may be used at the location of team 104 to display a picture of team 100 at step 615. At step 620, team 100 players grip and pull on rope 101 that connects to an electric winch 204 that applies a countering force on rope 101. At step 625, team 104 players grip and pull on rope 105 that connects to an electric winch that applies a countering force on rope 105. At step 630, the force applied by team 100 is measured by tensiometer 203, attached to a wire leading from the rope to a motor. At step 635, the force applied by team 104 is measured by a tensiometer, attached to a wire leading from rope 105 to a motor. At step 640, a signal is provided by the tensiometer 203 to computer 207 transmitting force data. Computer 207 uses the input to help determine the amount of torque it will command the electric winch, through a motor controller, to exert. At step 645, a signal is provided by a tensiometer to a computer transmitting force data exerted by team 104. This computer also uses the input to help determine the amount of torque it will command the electric winch, through a motor controller, to exert. At step 650, computer 207, at the location of team 100, provides data to the remote location where a force must be applied to rope 105 held by team 104. At step 655, a computer, at the location of team 104, provides data to the location of team 100, where a force must be applied to rope 101 held by team 100. At step 660, computer 207 determines the counterforce to be applied by the electric winch to rope 101 held by team 100, based on the pulling force of team 104 on their rope 105, and transmits a signal to the winch that applies the force on the rope. At step 665, a computer determines the counterforce to be applied by the electric winch to rope 105 held by team 104, based on the pulling force of team 100 on their rope 101, and transmits a signal to the winch that applies the force on the rope. If one side has won at step 690, the tug of war game ends at step 695. If there is no winner at step 690, the process is repeated beginning at steps 610 and 615.

Safety

The present invention also provides safety considerations that are not possible in actual tug of war. The computer can detect any sudden change in the force being applied to its own rope or the rope of the other team. If the sudden change in force could result in a dangerous condition, such as overspeed of the rope in one direction, the motor provides appropriate tension to prevent accidents. Thus, if one member of a team should let go of the rope, meaning the force on the rope applied by the remaining members is substantially less, the computer will prevent a sudden and violent pulling on the rope by the winch assembly. Similarly, when such occurs in a competition, the other team, suddenly encountering significantly reduced force, could suddenly fall backwards due to the lack of counterforce. Governors or limiters may be implemented in the winch and/or computer programming to prevent rope travel in any direction greater than some predetermined speed or distance.

Portability

The invention is such that it is suitable for portable operation. In particular, A truck or trailer can be used as a competition platform, with the rope/motor/computer system permanently mounted in the truck. The assembly can then be driven or towed to various locations for entertainment or competition. Even in the portable environment, a telecommunications link can be established with other assemblies, both fixed and portable.

Thus, a method and apparatus for implementing a virtual tug of war is described.

What is claimed is:

1. A device for playing a game of tug of war comprising:

a first rope for gripping by one or more first opponents;

a first force application mechanism adapted to apply a counter-force to said first rope dependent upon an opposing force applied by one or more second opponents;

a first display for displaying said one or more second opponents to said one or more first opponents, said first rope extending through said first display;

a first camera for obtaining images of said one or more first opponents;

a first tensiometer for measuring a force applied by said one or more first opponents;

a second rope located at a location remote to said first rope, said second rope for gripping by said one or more second opponents;

a second force application mechanism adapted to apply a counter-force to said second rope dependent upon an opposing force applied by said one or more first opponents;

a second display for displaying said one or more first opponents to said one or more second opponents, said second rope extending through said second display;

a second camera for obtaining images of said one or more second opponents;

a second tensiometer for measuring a force applied by said one or more second opponents;

a communications link for transmitting information representing images of said one or more first and second opponents obtained by said first camera for display by said second display and by said second camera for display by said first display, and for transmitting information representing said opposing force applied by said one or more second opponents and said opposing force applied by said one or more first opponents, wherein said opposing force applied by said second opponents comprises said counterforce to be applied to said first rope, and wherein said force applied by said first opponents comprises said counter-force to be applied to said second rope.

* * * * *